(12) United States Patent
Song

(10) Patent No.: US 10,403,117 B2
(45) Date of Patent: Sep. 3, 2019

(54) WATER QUALITY MEASUREMENT APPARATUS AND METHOD

(71) Applicant: Moen Incorporated, North Olmsted, OH (US)

(72) Inventor: Inho Song, Cleveland, OH (US)

(73) Assignee: MOEN INCORPORATED, A DELAWARE CORPORATION, North Olmsted, OH (US)

(*) Notice: Subject to any disclaimer, the term of this patent is extended or adjusted under 35 U.S.C. 154(b) by 2 days.

(21) Appl. No.: 15/639,952

(22) Filed: Jun. 30, 2017

(65) Prior Publication Data

US 2018/0005507 A1  Jan. 4, 2018

Related U.S. Application Data

(60) Provisional application No. 62/357,703, filed on Jul. 1, 2016.

(51) Int. Cl.
   *G01K 13/02* (2006.01)
   *G08B 21/18* (2006.01)
   (Continued)

(52) U.S. Cl.
   CPC ............ *G08B 21/182* (2013.01); *G01K 13/02* (2013.01); *G01N 27/302* (2013.01);
   (Continued)

(58) Field of Classification Search
   CPC .. G08B 21/182; G01N 27/48; G01N 27/4167; G01N 27/302; G01K 13/02; G01K 2013/026
   (Continued)

(56) References Cited

U.S. PATENT DOCUMENTS 4,849,098 A * 7/1989 Wilcock ............... B01D 61/12
                                                  210/85
5,646,863 A * 7/1997 Morton ................. G01N 33/18
                                                  210/688
(Continued)

FOREIGN PATENT DOCUMENTS

| CN | 103513014 A | * 1/2014 |
| CN | 105190302 A | 12/2015 |
| WO | 2016090176 A1 | 6/2016 |

OTHER PUBLICATIONS

International Search Report and Written Opinion for PCT/US2017/040433 dated Oct. 13, 2017.
(Continued)

*Primary Examiner* — Eric Blount
(74) *Attorney, Agent, or Firm* — Calfee, Halter & Griswold LLP

(57) ABSTRACT

A water quality measurement apparatus is provided. The apparatus comprises an electrochemical cell, a pH sensor, a temperature sensor, a control circuit, a power source, a database, and a warning device. The electrochemical cell comprises a working electrode, a reference electrode, and a counter electrode. The control circuit provides predetermined adjustable potentials between the reference electrode and the working electrode and measures electrochemical currents between the working electrode and the counter electrode, to form a current diagram based on the predetermined adjustable potentials and the electrochemical currents. The database stores predetermined reference diagrams based on various pH values and temperatures, and is in communication with the control circuit. The warning device is configured to output warnings, wherein the control circuit triggers the warning device in the condition that the current diagram exceeds the predetermined reference diagram based on the same range of the pH values and the temperatures.

7 Claims, 5 Drawing Sheets

(51) Int. Cl.
  *G01N 27/30* (2006.01)
  *G01N 27/42* (2006.01)
  *G01N 27/48* (2006.01)
  *G01N 33/18* (2006.01)
  *G01N 27/416* (2006.01)
  *G01F 1/00* (2006.01)
  *G01N 27/27* (2006.01)

(52) U.S. Cl.
  CPC ......... *G01N 27/4167* (2013.01); *G01N 27/42* (2013.01); *G01N 27/48* (2013.01); *G01N 33/1813* (2013.01); *G01F 1/00* (2013.01); *G01K 2013/026* (2013.01); *G01N 27/27* (2013.01)

(58) Field of Classification Search
  USPC .......................................................... 340/603
  See application file for complete search history.

(56) References Cited

U.S. PATENT DOCUMENTS

| | | | | |
|---|---|---|---|---|
| 6,398,930 | B2* | 6/2002 | Fukunaga | C02F 1/008 204/409 |
| 7,897,032 | B2* | 3/2011 | Viltchinskaia | G01N 33/1813 204/409 |
| 2003/0019748 | A1* | 1/2003 | Viltchinskaia | G01N 33/1813 204/400 |
| 2007/0278096 | A1* | 12/2007 | Viltchinskaia | G01N 33/1813 204/400 |
| 2009/0123340 | A1* | 5/2009 | Knudsen | G01N 33/1886 422/105 |
| 2016/0238583 | A1* | 8/2016 | Kodzius | G01N 27/48 |
| 2017/0363572 | A1* | 12/2017 | Gunasekaran | G01N 27/4167 |

OTHER PUBLICATIONS

Herzog et al., Determination of Trace Metals by Underpotential Deposition-Stripping Voltammetry at Solid Electrodes; Trac Trends in Analytical Chemistry, Elsevier, Amsterdam, NL, vol. 24, No. 3, Mar. 1, 2005 pp. 208-217.

* cited by examiner

WATER QUALITY MEASUREMENT APPARATUS AND METHOD

CROSS REFERENCE TO RELATED APPLICATION

This application claims the benefit of U.S. Provisional Application No. 62/357,703, filed Jul. 1, 2016, the entire disclosure of which is hereby incorporated by reference.

FIELD

The present subject matter relates generally to water quality measurement, and, more particularly, to a drinking water quality measurement for households.

BACKGROUND

The quality of municipal drinking water has continuously increased in the past decades. Yet, there is a growing need for detecting any upset conditions that would result in the introduction of harmful inorganic substances, such as lead, arsenic, cadmium, etc. Accurate and precise measurements of such are readily achieved in laboratories using expensive analytical equipment, such as ICP-MS. Not only is it expensive, the analysis requires a specially trained person and elaborate calibration and measurement procedures. This, therefore, is cost prohibitive for everyday home use by ordinary home owners.

SUMMARY

The present subject matter discloses a water quality measurement apparatus. The apparatus comprises an electrochemical cell, a pH sensor, a temperature sensor, a control circuit, a power source, a database, and a warning device. The electrochemical cell comprises a working electrode, a reference electrode, and a counter electrode, wherein the working electrode, the reference electrode, and the counter electrode are configured to be inserted into water to be detected. The pH sensor detects pH values of the water and provides a pH signal reflecting the pH values of the detected water to the control circuit. The temperature sensor detects temperatures of the water, and provides a temperature signal reflecting the temperatures of the detected water to the control circuit. The control circuit is electrically connected to the electrochemical cell, the pH sensor, and the temperature sensor. The control circuit provides predetermined adjustable potentials between the reference electrode and the working electrode and measures electrochemical currents between the working electrode and the counter electrode, to form a current diagram based on the predetermined adjustable potentials and the electrochemical currents. The power source provides power to the control circuit. The database stores predetermined reference diagrams based on various pH values and temperatures, and is in communication with the control circuit. The warning device is electrically connected to the control circuit and is configured to output warnings, wherein the control circuit triggers the warning device in the condition that the current diagram exceeds the predetermined reference diagram based on the same range of the pH values and the temperature values.

DETAILED DESCRIPTION

Features and advantages of the general inventive concepts will become apparent from the following detailed description made with reference to the accompanying drawings.

As used herein, when a test (or current) diagram is said to "exceed" a reference diagram, it is to be understood that a parameter calculated from the dataset associated with the test (or current) diagram exceeds a parameter calculated from the dataset associated with the reference diagram. Techniques for comparing a peak in a dataset with a reference peak are well known in the field of materials science, for example in the field of energy dispersive X ray analysis, Fourier transform infrared radiation analysis and the like.

The present subject matter provides an apparatus and a method of gauging the quality of water from the standpoint of contamination, such as heavy metal contamination, without requiring expensive equipment or requiring a trained operator.

The present subject matter utilizes the principles of electroplating and deplating. Electroplating is a process that uses electric current to reduce dissolved metal cations so that they form a thin coherent metal coating on an electrode. Deplating is the process in which some metal which is present as a layer above the other metal is removed from it. Usually the process of electrolysis is used. The process used in electroplating is called electrodeposition. Electroplating or electrodeposition is analogous to a galvanic cell acting in reverse. Both the cathode and the anode are disposed into the solution. When a power supply supplies a negative current to an electrode, i.e., the cathode, the dissolved metal ions in the electrolyte solution are reduced at the interface between the solution and the cathode, such that they "plate out" onto the cathode. When a power supply supplies a positive current to an electrode, i.e. the anode, the current oxidizes the metal atoms that the anode comprises and allows them to "be deplated" in the solution. Therefore, after measuring the current through the circuit, it can be calculated how many electrons are used for plating at the cathode or deplating at the anode. Since the water to be detected is drinking water, the possible harmful metal contaminants are limited. Often there is only a single kind of metal contaminant in the detected water. Therefore, the measured current is able to be directly converted to the number of contaminant metal atoms, which is then used to calculate the metal contaminant level.

Figure 1:
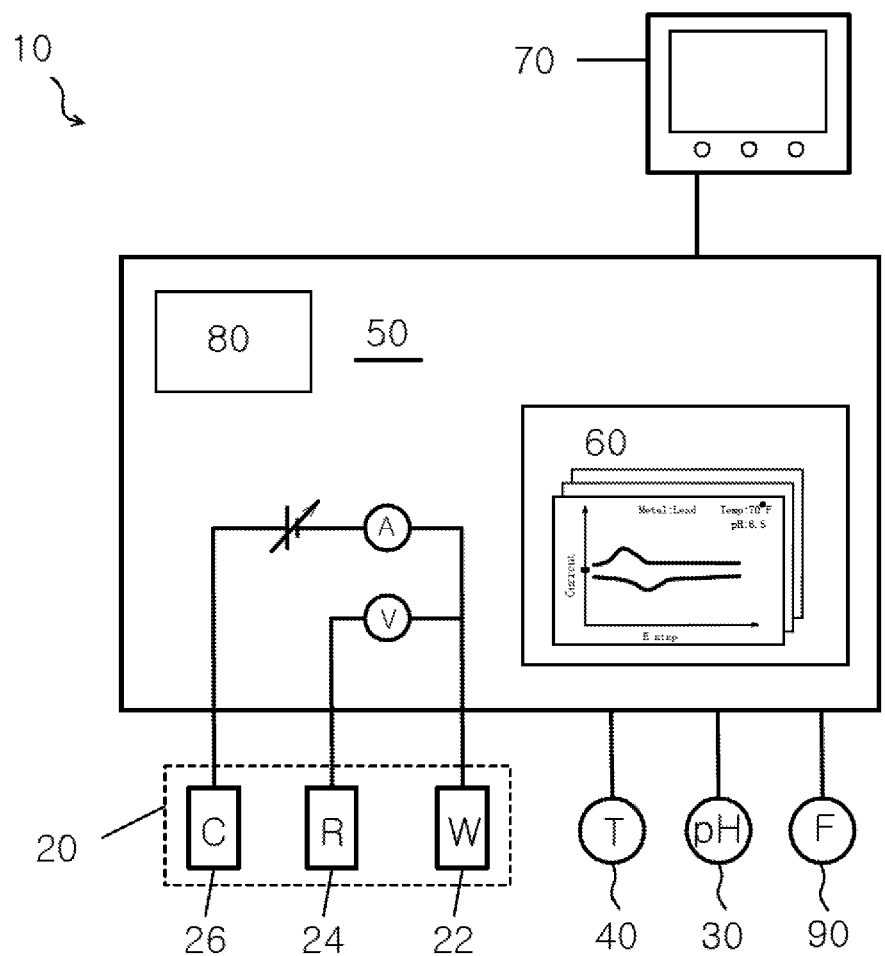
FIG. 1 is a schematic of an exemplary embodiment of a water quality measurement apparatus of the present subject matter.

One exemplary embodiment of a water quality measurement apparatus 10 of the present subject matter is shown in detail in FIG. 1. In the illustrated embodiment, the apparatus 10 comprises an electrochemical cell 20, a pH sensor 30, a temperature sensor 40, a control circuit 50, a database 60, a warning device 70, and a power source 80. The control circuit 50 is electrically connected to the electrochemical cell 20, the pH sensor 30, the temperature sensor 40, and the warning device 70.

The electrochemical cell 20 comprises a working electrode 22, a reference electrode 24, and a counter electrode 26. The working electrode 22, the reference electrode 24, and the counter electrode 26 are configured to be inserted into water to be detected. The working electrode 22 is gold in one exemplary embodiment. The counter electrode 26 is gold in one exemplary embodiment. The working electrode 22 is the location where plating and deplating are made to occur. The counter electrode 26 is the electrode that works with the working electrode 22 to permit an outside source to inject electrical current into the electrochemical cell 20 or receive it from the electrochemical cell 20. The reference electrode 24 is the reference point relative to which the electrochemical potential of the working electrode 22 is measured. In some embodiments, this reference electrode 24 is also used with the pH sensor 30 for measuring proton activity.

The pH sensor 30 is inserted into the water and detects pH values of the water. The pH sensor 30 provides a pH signal reflecting the pH values of the detected water to the control circuit 50. The pH signal can be digital or analog.

The temperature sensor 40 detects temperatures of the water and provides a temperature signal reflecting the temperatures of the detected water to the control circuit 50. The temperature signal can be digital or analog. The temperature sensor 40 may or may not directly contact the water.

The control circuit 50 provides predetermined adjustable potentials between the reference electrode 24 and the working electrode 22. When a negative potential is applied on the working electrode 22, the metal ions in the water plate on the working electrode 22. When a positive potential is applied on the working electrode 22, the metal atoms on the working electrode 22 deplate into the water. In some embodiments, the control circuit 50 may have two working modes, comprising a standby mode and a periodic mode. In some embodiments, the control circuit 50 may have two working modes, comprising the standby mode and a scan mode. In some embodiments, the control circuit 50 may have three working modes, comprising the standby mode, the periodic mode, and the scan mode. A person skilled in the art should readily understand that the control circuit 50 may have less than two working modes or more than three working modes. The periodic mode and the scan mode are detecting modes. The control circuit 50 can periodically maintain or scan the electrochemical potential of the working electrode 22 as desired. The control circuit 50 measures electrochemical currents between the working electrode 22 and the counter electrode 26. By using the predetermined adjustable potentials and the electrochemical currents, the control circuit 50 periodically forms a current diagram.

Figure 2:
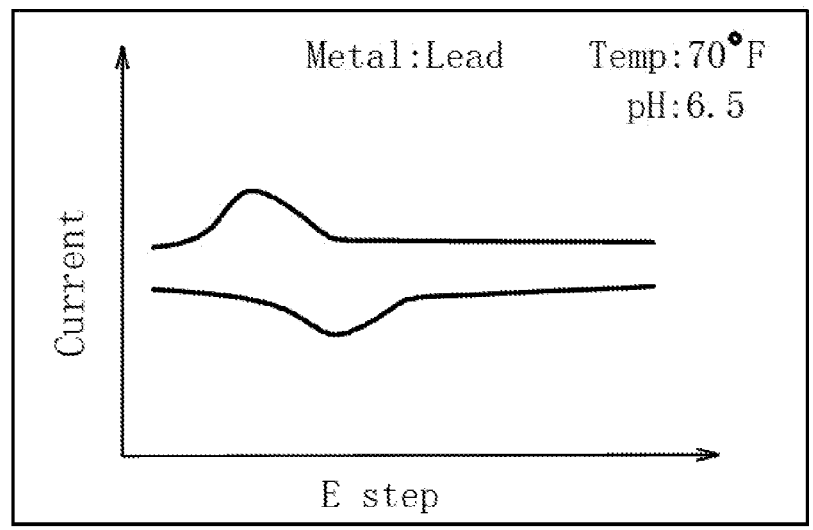
FIG. 2 is an exemplary embodiment of a current diagram stored in a database.

The database 60 is in communication with the control circuit 50. The database 60 can be stored in the control circuit 50, or be stored remotely. The database 60 stores predetermined reference diagrams. FIG. 2 is an exemplary reference diagram. As discussed above, the electrodeposition phenomenon is affected by the condition of the solution, such as the pH and the temperature. Therefore, each reference diagram comprises a current chart reflecting safety threshold(s) based on various suspicious metal contaminations, pH values, and temperatures.

The warning device 70 is configured to output warnings. The control circuit 50 triggers the warning device 70 in the condition that the current diagram exceeds the predetermined reference diagram based on the same range of the pH values and the temperature values. In some embodiments, the warning device 70 is a three-tier warning system, including a safe level, a questionable level, and an unacceptable level. When the current diagram does not exceed any thresholds, the warning device does not show any warnings, or shows a safe sign. When the current diagram exceeds a lower threshold, the warning device 70 shows a first warning to caution the user for drinking. When the current diagram exceeds a higher threshold, the warning device 70 shows a second warning to warn the user to stop using the water and to contact water authorities. For example, if the water is good, the warning device 70 displays a green light indicating the condition of safe consumption of water. If the measurement level exceeds the limit, but is within the band of statistical uncertainty (i.e., it exceeds the lower threshold, but is lower than the higher threshold), the warning device 70 displays a yellow light cautioning the user for drinking. However, in the event of an undesirable upset (i.e., it exceeds the higher threshold), the warning device 70 will display a red alarm indicating the user should stop using the water and contact the water authorities. The warning device can have a preset function that automatically contacts the water authorities through wired or wireless communications. The warning device 70 can be a built-in component that is physically attached to the control circuit 50 or a remote device, which communicates with the control circuit 50 through wired or wireless communications.

The power source 80 provides power to the control circuit 50 and subsequently to components of the apparatus 10 as desired. The power source 80 may be an AC-DC power source, solar cell, battery, or any kind of suitable power source.

In some embodiments, the control circuit 50 limits the electrochemical potentials of the working electrode 22 to be less negative than the equilibrium (Nernst) potential for the reduction of the suspicious metal. The phenomenon of deposition at a potential higher than the Nernst potential is known as underpotential deposition (UPD). In contrast to regular deposition, i.e., deposition at a potential below the Nernst potential, UPD is capable of depositing at most only a single monolayer of plated material onto the substrate. UPD is workable in the current subject matter the water analyzed here is drinking water. The contaminant level is relatively low, often only a few parts per billion. There is no need to deposit more than a single layer of contaminant metal of interest. Underpotential deposition helps to avoid generating hydrogen gas during deplating or oxygen gas during plating. In addition, underpotential deposition saves a lot of electrical energy considering the measurement works year-round.

Figure 3:
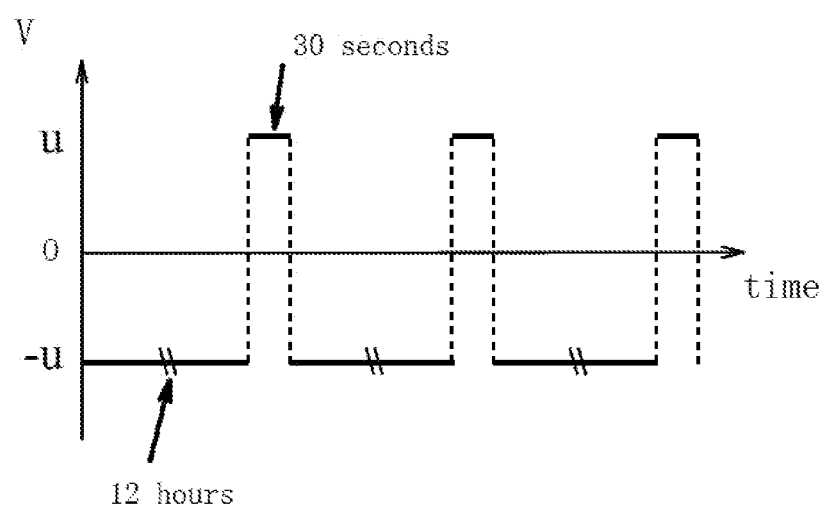
FIG. 3 is an exemplary embodiment of a voltage-time diagram of a periodic mode of a potential applied on a working electrode.
Figure 4:
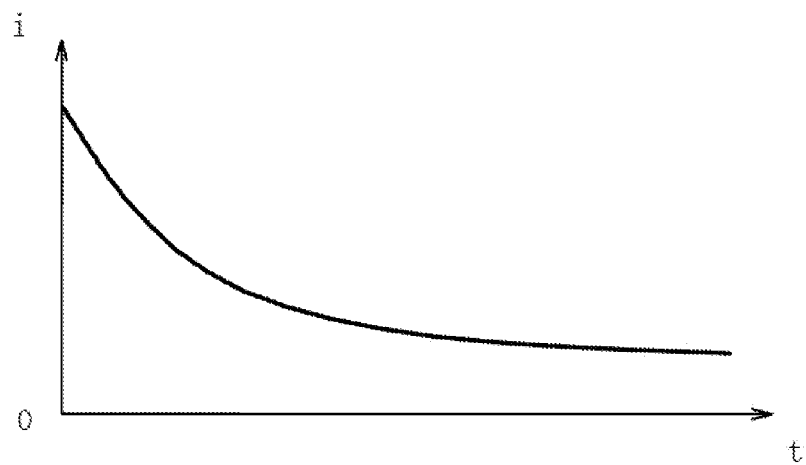
FIG. 4 is an exemplary embodiment of a current-time diagram of an electrochemical current under the periodic mode of FIG. 3.

The present subject matter discloses several methods for the control circuit 50 to periodically maintain or scan the adjustable potentials between the reference electrode 24 and the working electrode 22. For example, in one embodiment of the periodic mode, the control circuit 50 maintains periodic potentials on the working electrode 22, as shown in FIG. 3. A predetermined negative potential is applied to the working electrode 22 for a first predetermined time period, such as 12 hours, to plate contaminant metals. Then a predetermined positive potential is applied to the working electrode 22 for a second predetermined time period, such as 30 seconds, to deplate the metal. The control circuit 50 generates the current diagrams based on the electrochemical currents during deplating, which indicates how many metal atoms are accumulated within the last deposition period. One exemplary current diagram is shown as FIG. 4. This method is suitable for one or a few kinds of suspicious metal contaminants. The control circuit 50 applies a potential suitable for this kind of metal to the working electrode 22. The accumulated electrochemical current is measured. The number of metal atoms is calculated accordingly.

In some embodiments of the periodic mode, it is not necessary for the control circuit 50 to generate a real-time curve of the current diagram. The control circuit 50 may integrate the measured deplating current over a predetermined time period and compare it with the thresholds stored in the database 60.

Figure 5:
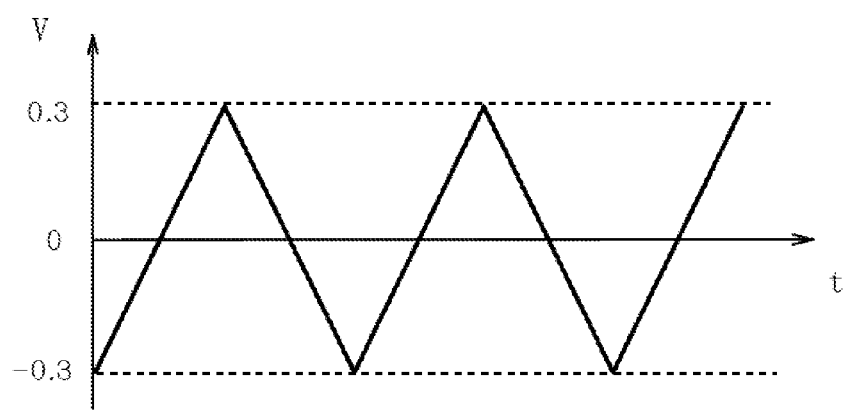
FIG. 5 is an exemplary embodiment of a voltage-time diagram of a scan mode of the potential applied on the working electrode.
Figure 6:
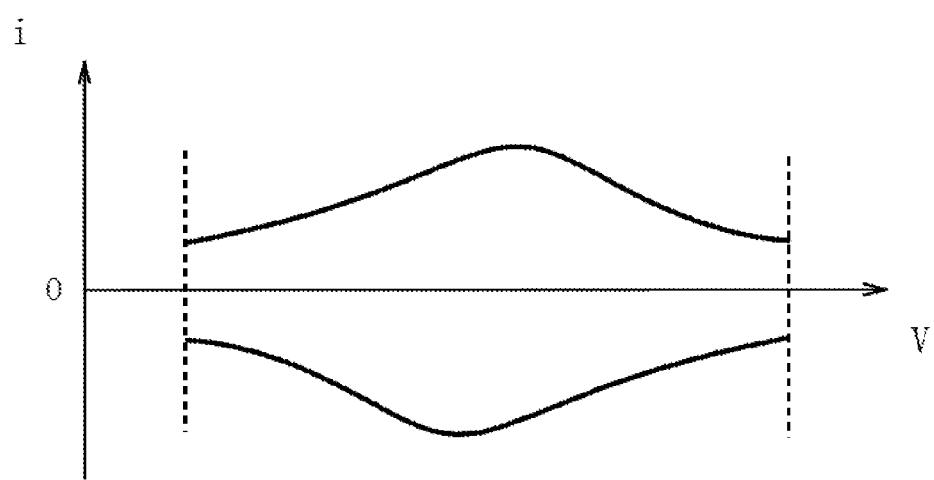
FIG. 6 is an exemplary embodiment of a voltammetry diagram of an electrochemical current under the scan mode of FIG. 5.

In another embodiment of the scan mode, the control circuit 50 scans cyclic potentials on the working electrode 22. The potential is cycled from a first voltage to a second voltage at a predetermined scan speed. For example, the potential is scanning from −0.3 volt to 0.3 volt at a speed of 0.1 volt per 10 seconds, as shown in FIG. 5. When the potential is negative, the working electrode 22 is plating. When the potential is positive, the working electrode 22 is deplating. By measuring the electrochemical current, the control circuit 50 may generate a voltammogram, as shown in FIG. 6. Since each metal is plated/deplated at a characteristic potential, the position of the current peak on the voltammogram may be used to identify the metal contaminant. The cyclic voltammogram generated by the control circuit 50 is compared with the database 60 to identify the metal contaminant and determine whether to trigger the warning device 70.

In some embodiments, the apparatus 10 further comprises a flow sensor 90. When measuring the contamination level, the flow rate of the water is an important factor. Within the same time period, different flow rates of the same water may cause different amounts of metal to be plated on the working electrode 22. In addition, the flow sensor 90 can be used as a switch for the apparatus 10 under the scan mode. When the user is not using the water, the water in the piping system is quiescent. Thus, it may be meaningless and misleading to continuously scan and to measure the water quality when the water is not in use. Therefore, in some embodiments, the apparatus 10 is held in the standby mode, when the water flow rate is lower than a predetermined threshold. Only when the flow rate of the water exceeds a predetermined threshold, the control circuit 50 starts its detecting mode and scans the potential, generates the current diagram, and compares with the database 60.

Figure 7:
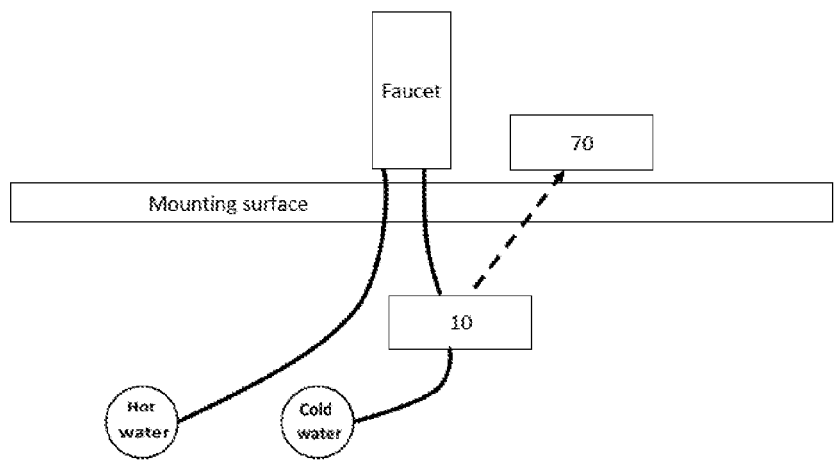
FIG. 7 is an exemplary embodiment of a water quality measurement apparatus separated from a faucet.
Figure 8:
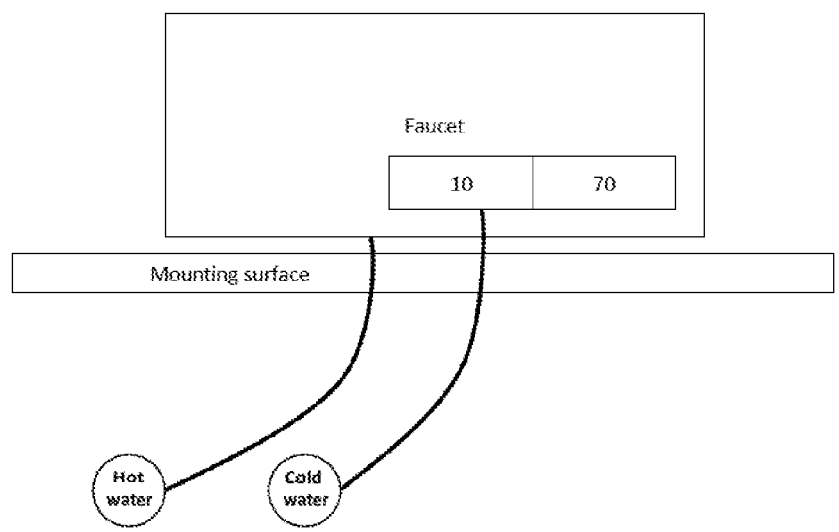
FIG. 8 is an exemplary embodiment of a water quality measurement apparatus incorporated into a faucet.

In an exemplary embodiment, the water quality measurement apparatus is a stand-alone device in a water system, such as a residential or commercial water system. As shown in FIG. 7, the water quality measurement apparatus is located below a mounting surface for a plumbing fixture fitting, such as a faucet. Alternatively, the water quality measurement apparatus could be located above the mounting surface or at a central location in the water system, such as at an incoming supply line for the water system. In another exemplary embodiment as shown in FIG. 8, the water quality measurement apparatus is incorporated into a plumbing fixture fitting, such as a faucet.

In view of the many possible embodiments to which the principles of the disclosed invention can be applied, it should be recognized that the illustrated embodiments are only exemplary examples of the invention and should not be taken as limiting the scope of the invention. All combinations or subcombinations of features of the foregoing exemplary embodiments are contemplated by this application.

The scope of the invention is defined by the following claims. I therefore claim as my invention all that comes within the scope and spirit of these claims.

The invention claimed is:

1. A water quality measurement apparatus, comprising:
an electrochemical cell, comprising a working electrode, a reference electrode, and a counter electrode, wherein the working electrode, the reference electrode, and the counter electrode are configured to be inserted into water to be detected,
a pH sensor, configured to detect pH values of the water and to provide a pH signal reflecting the pH values of the detected water to a control circuit,
a temperature sensor, configured to detect temperatures of the water, and to provide a temperature signal reflecting the temperatures of the detected water to the control circuit,
the control circuit, electrically connected to the electrochemical cell, the pH sensor, and the temperature sensor, wherein the control circuit is configured to provide predetermined adjustable potentials between the reference electrode and the working electrode and to measure electrochemical currents between the working electrode and the counter electrode, to periodically form a current diagram based on the predetermined adjustable potentials and the electrochemical currents,
a power source, providing power to the control circuit,
a database, storing predetermined reference diagrams based on various pH values and temperatures, and being in communication with the control circuit, and
a warning device, being in communication with the control circuit and configured to output warnings, wherein the control circuit triggers the warning device in the condition that the current diagram exceeds the predetermined reference diagram based on the same range of the pH values and the temperature values,
wherein the predetermined adjustable potentials are underpotentials.

2. The water quality measurement apparatus of claim 1 further comprising a flow sensor, electrically connected to the control circuit, and configured to detect flow rates of the water and to provide a flow rate signal reflecting the flow rates of the detected water to the control circuit, wherein the control circuit calibrates the current diagram based on the flow rates.

3. The water quality measurement apparatus of claim 2, wherein the control circuit is at its standby mode when the flow rate is lower than a predetermined threshold; the control circuit is at its detecting mode when the flow rate is higher than the predetermined threshold.

4. The water quality measurement apparatus of claim 1, wherein the control circuit provides a first predetermined adjustable potential for a first time period and a second predetermined adjustable potential for a second time period, wherein the current diagram is a time-current diagram formed during the second time period.

5. The water quality measurement apparatus of claim 4, wherein the first predetermined adjustable potential is opposite to the second predetermined adjustable potential.

6. The water quality measurement apparatus of claim 1, wherein the predetermined adjustable potentials are cyclic voltammetry potentials.

7. The water quality measurement apparatus of claim 1, wherein the current diagram is a cyclic voltammetry diagram.

* * * * *